United States Patent [19]

Kakeya et al.

[11] 4,260,607
[45] Apr. 7, 1981

[54] CEPHALOSPORIN ESTERS

[75] Inventors: Nobuharu Kakeya, Kawanishi; Yoshinobu Yoshimura, Osaka, both of Japan

[73] Assignee: Takeda Chemical Industries, Ltd., Osaka, Japan

[21] Appl. No.: 76,545

[22] Filed: Sep. 18, 1979

Related U.S. Application Data

[63] Continuation of Ser. No. 819,620, Jul. 27, 1977, abandoned.

[30] Foreign Application Priority Data

Aug. 10, 1976 [JP] Japan .................................. 51/95849

[51] Int. Cl.³ .......................................... C07D 501/36
[52] U.S. Cl. ...................................... 424/246; 544/27; 544/21; 544/26
[58] Field of Search .................... 424/246; 544/26, 21, 544/27

[56] References Cited

U.S. PATENT DOCUMENTS

| | | | |
|---|---|---|---|
| 4,008,246 | 2/1977 | Ochiai et al. | 544/27 |
| 4,080,498 | 3/1978 | Numata et al. | 544/27 |

*Primary Examiner*—Nicholas S. Rizzo
*Attorney, Agent, or Firm*—Craig and Antonelli

[57] ABSTRACT

A cephalosporin derivative of the formula:

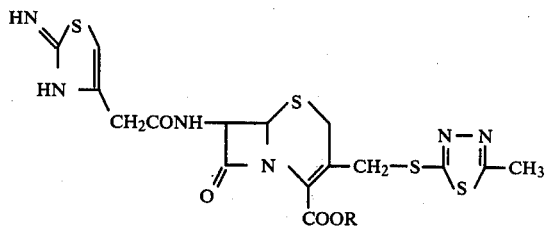

wherein R represents

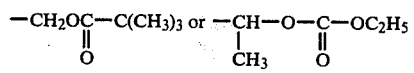

or its pharmaceutically acceptable acid addition salt is found to be useful as orally administrable antibiotics having broad anti-microbial activities against both Gram-positive and Gram-negative bacteria.

5 Claims, No Drawings

CEPHALOSPORIN ESTERS

This is a continuation of application Ser. No. 819,620, filed July 27, 1977 now abandoned.

This invention relates to cephalosporin derivatives of the formula:

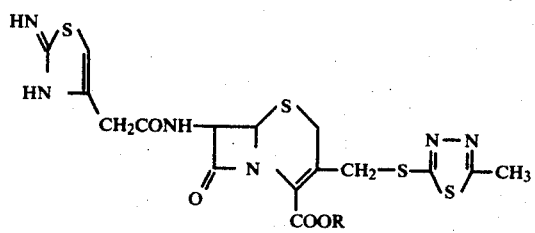

wherein R represents

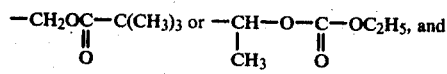

to a process for producing the same.

As the result of various investigations made by the present inventors, it has been found that the above cephalosporin derivatives (I) can well be absorbed from gastro-intestinal tract and hydrolyzed rapidly after absorption by enzymes in a body at 4-position carboxylic ester with liberation of non-ester compounds corresponding to the compounds (I) thereby to attain high blood-levels of the non-ester compounds enough for medical treatment; that they can therefore be useful as orally administrable anti-biotics having broad anti-microbial activities against Gram-positive bacteria, Gram-negative bacteria or both thereof; and further that the acid addition salts of the present compounds (I) can increase water-solubility of esters to improve absorption efficiency and stabilize the compounds (I), whereby isolation and pelletizing of said compounds can be made easier.

The compounds (I) are per se basic in nature and hence may sometimes by unstable in free form. They can therefore be converted, if necessary, to acid addition salts. As preferable non-toxic acids suitable for such acid addition salts, there may be mentioned mineral acids such as hydrochloric acid, sulfuric acid, phosphoric acid and the like, and organic acids such as maleic acid, acetic acid, citric acid, succinic acid, benzoic acid, fumaric acid, malonic acid, mandelic acid, ascrobic acid and the like. These acid addition salts are also included within the cephalosporin derivatives (I).

The cephalosporin derivatives (I) can be produced by per se known methods. For example, they can be produced according to the processes as shown below:

PROCESS 1

This process comprises reacting a compound of the formula (II):

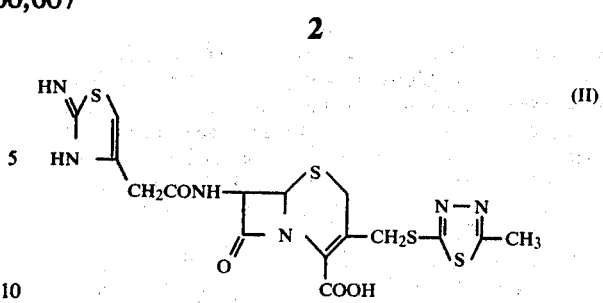

with a compound of the formula ROH (wherein R is the same as defined above), namely (III-a) or (III-b):

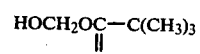

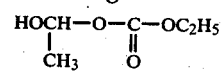

In carrying out the reaction of this process, the imino group of the compound (II) is usually preferred to be protected. The protected imino group means a protected imino group which is once protected during the esterification reaction and can be afterwards converted again, if desired, to the original imino group. For example, there may frequently be used protonated imino group; 2,2,2-trifluoroethoxycarbonyl imino group which can be restored by reduction; 2-alkyl- or aryl-sulfonylethloxycarbonyl imino group (e.g. 2-methylsulfonylethyloxycarbonyl imino group) which can be restored within a short time by alkali treatment; or t-butoxycarbonyl imino group which can be restored by acid treatment. In carrying out the reaction, both of the starting compounds can be used in free form, but it is more convenient to use one or both of them as reactive derivatives for esterification. The reactive derivatives of cephalosporin compounds (II) can be produced by converting 4-carboxyl group thereof to reactive derivatives. Namely, said reactive derivatives mean carboxylic acid derivatives which can form ester bonds in condensation between carboxylic acids and alcohols. For example, there may be used inorganic salts with alkali metals such as sodium or potassium; organic salts with organic amines such as triethylamine or dicyclohexyl amine; acid halides such as acid bromide; acid anhydrides; lower aliphatic mono-esters of carbonic acid (e.g. ethyl carbonate, isopropyl carbonate); alkyl sulfonates (e.g. methane sulfonate); aryl sulfonates (e.g. p-toluene sulfonate); mixed acid anhydrides composed of strong acids suffering from steric hindrance such as diphenylacetic acid; intermediates formed with carbodiimide reagents (e.g. N,N'-carbonyldiimidazole, N,N-carbonylditriazole, N,N-dimethylchloroformiminium-chloride); etc. The reactive derivatives for esterification of the compounds (III-a) or (III-b) are exemplified by alkyl- or aryl-sulfonyl esters (e.g. methyl sulfonyl ester, p-toluenesulfonyl ester); diesters with sulfuric or sulfurous acid; alkyl- or aryl-chloroformate to be esterified with decarbonization (e.g. ethylchloroformate, phenyl-chloroformate); alkoxy- or aryloxy-sulphenyl and sulfonylchloride to be esterified with elimination of sulfur dioxide or sulfur trioxide; or halides wherein hydroxyl group of the compound (III-a) or (III-b) is substituted by a halogen such as chlorine, bromine or iodine. In order to avoid formation of $66^2$-isomer as by-product, the reaction is preferably carried out by using, for example, a salt of the compound (II) or a halide of the compound (III-a) or (III-b) at room temperature or, if necessary, with cooling or heating. The reaction can be allowed to proceed readily in the presence of a solvent inert to the reaction such as dimethylformamide (DMF), dimethylacetamide (DMA), hexamethyltriamidephosphate (HMPA), acetone, acetonitrile, etc. After esterification, if necessary, the protective groups of the protected imino group can be eliminated by per se known method to give the cephalosporin derivative (I).

PROCESS 2

According to another process, the compound (I) can be prepared by first reacting the compound of the formula (II'):

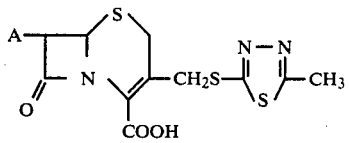

wherein A is amino group or an acylamino group excluding (2-amino-4-thiazolin-4-yl) acetamino group, with a compound of the formula (III-a) or (III-b) to carry out the reaction in the same manner as the esterification reaction as previously described, followed by, in case when A is an acylamino group, deacylation of the esterified product obtained by conventional method (as disclosed by Journal of Medicinal Chemistry, Vol. 18, p.992, 1975; German Patent Application laid-open Specification No. P2460331.4 and P2460332.5), to derive the compound of the formula (IV);

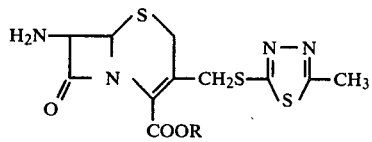

wherein R is as defined above, and then reacting the compound (IV) with the compound [(2-imino-4-thiazolin-4-yl)acetic acid] of the formula (V):

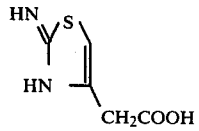

thereby to effect acylation of the amino group at 7-position of the compound (IV).

When A in the above formula (II') is an acylamino group, the acylamino group may be any one known per se in the art of cephalosporin compounds. Examples of the acyl-amino group are acetylamino, benzoylamino, phenylacetylamino, thienylacetylamino, phenyloxylacetylamino, 5-amino-5-carboxyvalerylamide, and so on. When A is amino group or an amino-containing acylamino group, the amino group is preferably protected during the reaction. As the protective group of the amino group, there may be used per se known protective groups of amino groups, including t-butoxycarbonyl, carbobenzyloxy, 2-hydroxyl-1-naphthocarbonyl, trichloroethoxycarbonyl, 2-ethoxycarbonyl-1-methylvinyl and 2-methoxycarbonyl-1-methylvinyl. The imino group of the compound (V) is preferably protected during the reaction. This protective group may be the same as that of the imino group in the compound (II). The compound (V) can be used either in free form or in the form of a reactive derivative thereof. Namely, it can be provided for acylation reaction either as free acid, as a salt with sodium, potassium, calcium, trimethylamine, pyridine, etc., or as a reactive derivative thereof such as acid halide, acid anhydride, mixed acid anhydride, active amide, ester, etc. As an active ester, there may be used p-nitrophenyl ester, 2,4-dinitrophenyl ester, pentachlorophenyl ester, N-hydroxyphthalimide ester, etc. As a mixed acid anhydride, there may be used a mixed acid anhydride with mono-ester carbonates such as mono-methyl carbonate, mono-isobutyl carbonate or a mixed acids anhydride with lower alkanoic acids which may be substituted by halogens such as pivalic acid or trichloroacetic acid.

When the compound (V) is used in its free form or an acid form, there is used a condensing agent as exemplified by N,N'-disubstituted carbodiimides such as N,N'-dicyclohexylcarbodiimide; azolide compounds such as N,N'-carbonylimidazole or N,N'-thionyldiimidazole; dehydrating agents such as N-ethoxycarbonyl-2-ethoxy-1,2-dihydroquinoline, phosphorus oxychloride, alkoxy acetylene (e.g. ethoxy acetylene); and so on. When these condensing agents are used, the reaction is considered to proceed via a reactive derivative of carboxylic acid.

The present reaction can usually be practiced advantageously and smoothly in a solvent. As a solvent, there may be used any of the solvents in general which do not interfere with the reaction, or a mixture thereof, including water, acetone, diisobutyl ketone tetrahydrofuran, ethyl acetate, dioxane, acetonitrile, chloroform, dichloromethane, dichloroethylene, pyridine, dimethylaniline, dimethylformamide, dimethylacetamide, dimethylsulfoxide, and so on. The reaction temperature is not particularly limited, but the reaction is conducted usually under cooling or at room temperature. When the reaction proceeds with liberation of acids, bases are allowed to coexist, if desired. As such bases, there may generally be used aliphatic, aromatic or heterocyclic nitrogen bases or alkali metal carbonate or bicarbonates, for example, triethylamine, N,N'-dimethylaniline, N-ethyl morpholine, pyridine, collidine, 2,6-lutidine, sodium carbonate, potassium carbonate, sodium hydrogen carbonate and potassium hydrogen carbonate. When the acylation reaction proceeds perponderantly by way of dehydrating reaction, it is preferred to exclude water from the solvent. In some cases, the reaction may be operated in an inert gas such as nitrogen so as to be kept away from moisture.

PROCESS 3

According to still another process, the compound (I) can be produced by reacting the compound (IV) as mentioned above with 4-halogeno-3-oxobutyrylhalogenide, which is obtained by reacting diketene with equimolar amount of halogen (e.g. chlorine, bromine or iodine), to obtain the compound (IV) of the formula:

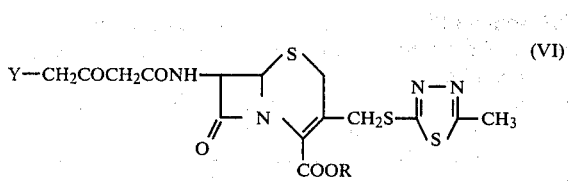

(VI)

wherein R is the same as defined above, and Y represents a halogen atom (e.g. chlorine, bromine or iodine atom), and then reacting the compound (VI) with thiourea. In the reaction between the compound (VI) and thiourea, thiourea can be provided for the reaction as it is or as a salt with an alkali metal such as lithium, sodium or potassium or an ammonium salt. The reaction is usually carried out by mixing equimolar amounts of both compounds and 1 to 2 equivalent of a base. As a solvent suitable for this reaction, there may be mentioned water, methanol, ethanol, acetone, dioxane, acetonitrile, chloroform, ethylene chloride, tetrahydrofuran, ethyl acetate, dimethylformamide, dimethylacetamide and other common organic solvents which do not interfere with the reaction. Among them, a hydrophilic solvent can be used in admixture with water. As a base to be used, there may be mentioned alkali metal hydroxides such as sodium hydroxide, potassium hydroxide, etc.; alkali metal carbonates such as sodium carbonate, potassium carbonate, etc.; alkali metal hydrogen carbonate such as sodium hydrogen carbonate; and organic tertiary amines such as trimethylamine, triethylamine, pyridine, etc. The base is used for the purpose of neutralizing carboxyl groups of cephalosporin and hydrohalogenic acid eliminated by the reaction. Thus, it is used usually in about 2 equivalent amount as free thiourea and in about 1 equivalent amount as an alkali metal salt, respectively. The reaction temperature is not particularly limited, but it is generally preferred to carry out the reaction under cooling. The reaction generally takes place rapidly and is completed usually within 10 minutes, but it may sometimes take more than 30 minutes before completion of the reaction.

When $\Delta^2$-isomer is co-present with the objective cephalosporin derivatives (I) in the reaction product obtained by these reactions, it may be isomerized, if necessary, by per se known method, for example, the method as disclosed in Journal of Medicinal Chemistry, Vol. 18, p. 986, 1975, into $\Delta^3$-isomer or converted to $\Delta^3$-isomer by leading to corresponding S-oxide thereof, followed by reduction of the $\Delta^3$-isomer to be reversed to the cephalosporin derivative (I) by conventional methods.

The objective compounds (I) can be isolated and purified according to conventional procedures. Since the compounds (I) are readily soluble in an organic solvent, they can usually be extracted with a solvent.

The thus obtained cephalosporin derivatives (I) can well be absorbed from gastro-intestinal tract and hydrolyzed rapidly after absorption at 4-position carboxylic ester with liberation of non-ester compounds, said non-ester compounds having broad antimicrobial spectrum against Gram-negative and Gram-positive bacteria. The compounds having antimicrobial activity against Gram-negative bacteria such as *Escherichia coli, Klebsiella pneumoniae, Proteus vulgaris* and *Proteus morganii* exhibit high blood-vessels by oral administration and can be used for the treatment of infections with these bacteria in mammals including human beings. The compounds (I) of the present invention are low in toxicity and can orally be administered. They can be admixed with diluents (e.g. starch, lactose, sucrose, calcium carbonate, calcium phosphate, etc.), binders (e.g. starch, gum arabic, carboxymethyl cellulose, hydroxypropyl cellulose, crystalline cellulose, etc.), lubricants (e.g. magnesium stearate, talc, etc.) or disintegrators (e.g. carboxymethyl calcium, talc, etc.) by conventional methods to be orally administered in the form of capsules, powders, granules, tablets, etc. for treatment of diseases caused by the aforesaid Gram-negative and Gram-positive bacteria, typically respiratory and urinary-tract infections in human beings. The dosage may be 0.3 to 5 g per adult human per day, preferably 1 to 3 g, by 3 to 4 divided doses, per day.

The compounds (II) to be used in the present invention can be produced by such methods as disclosed in German Patent Application, laid-open Specification No. 2461478.6 and No. 2607064.4; the compounds (II') by such methods as disclosed in German Patent Application, laid-open Specification No. 224620.4, No. 2460331.4 and No. 2460332.5, and German Patent Application No. 2607064.4. The compounds (III) can be produced by such methods as described in Journal of American Chemical Society, Vol. 43, p.660 (1921).

EXAMPLE 1

7β-(2-imino-4-thiazolin-4-yl)acetamido-3-(5-methyl-1,3,4-thiadizolyl-2-yl)thiomethyl-3-cephem-4-pivaloyloxymethyl carboxylate hydrochloric acid salt:

In 50 ml of dimethylformamide is dissolved 5.21 g of sodium 7β-(2-imino-4-thiazolin-4-yl)acetamido-3-(5-methyl-1,3,4-thiadiazolyl-2-yl)thiomethyl-3-cephem-4-carboxylate. While the solution is stirred at room temperature, 2.3 g of iodomethyl pivalate is added thereto. After 20 minutes, 200 ml of ethyl acetate and 300 ml of 0.1 M-NaHCO$_3$ are added for separation, and the ethyl acetate layer is washed with saturated aqueous sodium chloride solution, followed by drying with anhydrous sodium sulfate, and then subjected to filtration. The filtrate is mixed with 10 ml of 1 N ether solution of hydrochloric acid and concentrated to traces of ethyl acetate. The precipitated powders formed by addition of ether are recovered by filtration to give 5.91 g of the objective compound.

IR(KBr): 1785 cm$^{-1}$(β-lactam), 1750 cm$^{-1}$(ester)

NMR(d$_6$-DMSO/D$_2$O): δ1.18(s), 2.70(s), 3.61(s), 3.72(s), 4.15(d, J=13.2 Hz), 4.58(d, J=13.2 Hz), 5.11(d, J=5.4 Hz), 5.72(d, J=5.4 Hz), 5.81(d, J=6 Hz), 5.93(d, J=6 Hz), 6.62(s)

EXAMPLE 2

The compound of the following formula:

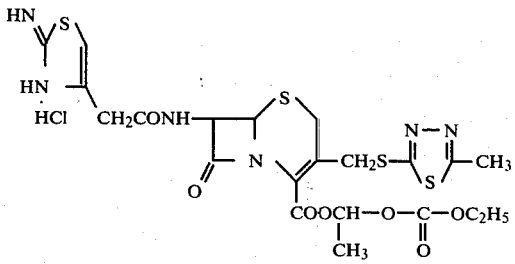

is prepared according to the similar procedure as described in Example 1.

IR(KBr): 1785 cm$^{-1}$(β-lactam), 1750 cm$^{-1}$(ester)

NMR(d$_6$-DMSO/D$_2$O): δ1.05(t, J=7 Hz), 1.26(d, J=7 Hz), 2.70(s), 3.62(s), 3.72(s), 3.92(q, J=7 Hz), 4.23(d, J=13 Hz), 4.45(d, J=13 Hz), 5.10(d, J=5 Hz), 5.75(d, J=5 Hz), 6.70(s)

EXAMPLE 3

To 20 ml of a dimethylformamide solution containing 1.58 g of (2-imino-4-thiazolin-4-yl)acetate hydrochloric acid salt are added 4.6 g of 7β-amino-3-(5-methyl-1,3,4-thiadiazolyl-5-yl)thiomethyl-3-cephem-4-pivaloyloxymethylcarboxylate and 2.06 g of dicyclohexylcarbodiimide. The mixture is stirred at room temperature and the resulting precipitated solids are removed by filtration. The filtrate is mixed with 100 ml of ethyl acetate and 130 ml of 0.1 M aqueous sodium hydrogen carbonate solution and the ethyl acetate layer separated is washed with saturated sodium chloride solution, followed by drying with anhydrous sodium sulfate, and then subjected to filtration. The filtrate is mixed with 1 N ether solution of hydrochloric acid and concentrated to traces of ethyl acetate. Addition of ether to the concentrate gives precipitated powders which are recovered by filtration to obtain 3.9 g of the objective compound. This product is found to be identical in IR and NMR with that obtained in Example 1.

The starting material 7β-amino-3-(5-methyl-1,3,4-thiadiazolyl-2-yl)-thiomethyl-3-cephem-4-pivaloyloxymethylcarboxylate is prepared in the following manner:

In 30 ml of a phosphate buffer solution with pH 6.4 are dissolved 3.14 g of 7β-amino-3-(3-oxobutyryloxy)-methyl-3-cephem-4-carboxylic acid, 1.32 g of 2-mercapto-5-methyl-1,3,4-thiadiazole and 1.68 g of sodium hydrogen carbonate, and the solution is heated at 50° C. for 1.5 hours. After cooling, the solution is subjected to column chromatography with polystyrene resin (Amberlite XAD-2) using water as eluant. The fractions containing the objective compound are lyophilized to obtain 2.72 g of sodium 7β-amino-3-(5-methyl-1,3,4-thiadiazolyl-2-yl)thiomethyl-3-cephem-4-carboxylate.

This product (3.45 g) is suspended in a mixture comprising 20 ml of water and 20 ml of dioxane and dissolved by adding 2 ml of triethylamine to the suspension, followed by addition of 2.4 g of 2-(t-butoxycarbonyl)thio-4,6-dimethylpyrimidine at 10° C., and the mixture is left to stand after stirring overnight. After evaporation of the solvent under reduced pressure, a small amount of water is added to the residue, which is then made acidic with 4 N-HCl and extracted with ethyl acetate. The ethyl acetate extract is washed with saturated aqueous sodium chloride solution, dried over anhydrous sodium sulfate and filtered. The filtrate is evaporated under reduced pressure. The resulting solid is suspended in water, neutralized with 1 N-NaOH and lyophilized to give 2.83 g of sodium 7β-(t-butoxycarbonyl)amino-3-(5-methyl-1,3,4-thiadiazolyl-2-yl)-thiomethyl-3-cephem-4-carboxylate.

This product (2.18 g) is dissolved in 20 ml of dimethylformamide and 1.23 g of iodomethyl pivalate is added to the solution. After stirring for 10 minutes, 100 ml of ethyl acetate and 150 ml of 0.1 N-NaHCO$_3$ are added for separation. The ethyl acetate layer is washed with saturated aqueous sodium chloride solution, dried over anhydrous sodium sulfate and evaporated under reduced pressure to remove the solvent. The residue is cooled on ice, diluted with 15 ml of trifluoroacetic acid and stirred. After 30 minutes, ether is added and the solids are recovered by filtration of obtain 1.21 g of 7β-amino-3-(5-methyl-1,3,4-thiadiazolyl-2-yl)thiomethyl-3-cephem-4-pivaloyloxymethylcarboxylate trifluoracetic acid salt. This product is dissolved in water, neutralized with 1 N-NaOH and extracted with ethyl acetate to give 1.18 g of 7β-amino-3-(5-methyl-1,3,4-thiadiazolyl-2-yl)thiomethyl-3-cephem-4-pivaloyloxymethylcarboxylate.

IR(KBr): 3200 cm$^{-1}$, 1793 cm$^{-1}$, 1750 cm$^{-1}$

NMR(in d$_6$-DMSO/D$_2$O): δ1.18(s), 2.69(s), 3.70(s), 4.15(d, J=13.2 Hz), 4.62(d, =13.2 Hz), 5.80(d, J=5 Hz), 5.83(d, =6 Hz), 5.99(d, J=6 Hz)

EXAMPLE 4

(1) A solution of 4.4 g of diketene in 4 ml of methylene chloride is cooled to −35° C. and a solution of 0.90 g of bromine in 1 ml of methylene chloride is added dropwise thereto. Into this solution is further added under stirring a solution of 1.52 g of 7β-amino-3-(5-methyl-1,3,4-thiadiazolyl-5-yl)thiomethyl-3-cephem-4-pivaloyloxymethylcarboxylate and 0.40 g of triethylamine in 10 ml of methylene chloride, which has been separately prepared under cooling at not over −30° C. The liquid temperature is elevated gradually over one hour up to room temperature and the reaction mixture is washed three times with 10% aqueous sodium chloride solution, dried and concentrated under reduced pressure. The precipitated powders formed by addition of hexane to the residue are recovered by filtration to give 1.3 g of 7β-(4-bromo-3-oxobutyrylamido)-3-(5-methyl-1,3,4-thiadiazolyl-5-yl)thiomethyl-3-cephem-4-pivaloyloxymethylcarboxylate.

IR(KBr): 1780 cm$^{-1}$, 1750 cm$^{-1}$, 1680 cm$^{-1}$

NMR(d$_6$-DMSO/D$_2$O): δ1.18(s), 2.70(s), 3.1–3.8 (m), 4.03(s), 4.15(d, J=13.2 Hz), 4.56(d, J=13.2 Hz), 5.00 (d, J=5 Hz), 5.70(d, J=5 Hz), 5.81(d, J=6 Hz), 5.90(d, J=6 Hz)

(2) To a solution of 3.0 g of 7β-(4-bromo-3-oxobutyrylamido)-3-(5-methyl-1,3,4-thiadiazolyl-2-yl) thiomethyl-3-cephem-4-pivaloyloxymethylcarboxylate in 15 ml of acetone is added 0.5 g of thiourea to be dissolved therein. After a while, the precipitated powders are recovered by filtration to obtain 1.8 g of 7β-(2-amino-4-thiazolin-4-yl)acetamido-3-(5-methyl-1,3,4-thiazolyl-2-yl) thiomethyl-3-cephem-4-pivaloyloxymethylcarboxylate hydrobromic acid salt.

IR(KBr): 1780 cm$^{-1}$, 1750 cm$^{-1}$

NMR(d$_6$-DMSO/D$_2$O): δ1.18(s), 2.70(s), 3.62(s), 3.72(s), 4.10(d,J=13.2 Hz), 4.59(d,J=13.2 Hz), 5.10(d,J=5.4 Hz), 5.72(d, J=5.4 Hz), 5.81(d,J=6 Hz), 5.93(d,J=6 Hz), 6.70(s)

EXAMPLE 5

The capsules having the following composition are prepared according to conventional technique:

| | |
|---|---|
| 7β-(2-imino-4-thiazolin-4-yl) acetamido-3-(5-methyl-1,3,4-thiadiazolyl-2-yl)thiomethyl-3-cephem-4-pivaloyloxymethyl-carboxylate hydrochloric acid salt: | 334 mg |
| Starch | 10 mg |
| Methyl cellulose | 7 mg |
| Magnesium stearate | 5 mg |
| | 356 mg/capsule |

EXAMPLE 6

Biological data

Cephalexin and the cephalosporin esters prepared in Examples 1 and 2 are administered orally to rats at a dose of 100 mg/kg to obtain the blood-vessels as shown in Table 1.

TABLE 1

Blood-level in rat
(meg/ml: average of three samples)

| Compound | Time (hours) | | | |
|---|---|---|---|---|
| | 0.5 | 1 | 2 | 4 |
| Example 1 | 31.8 | 29.3 | 22.0 | 8.7 |
| Example 2 | 32.4 | 28.3 | 21.0 | |
| Cephalexin | 26.3 | 28.9 | 16.3 | 7.9 |

Either of the compounds of Example 1 and Example 2 is hydrolyzed at 4-position carboxylic acid ester after being absorbed in blood to exist in the form of non-ester at 4-position of carboxylic acid of the corresponding cephalosporin compound.

MIC of the compound of the formula (A):

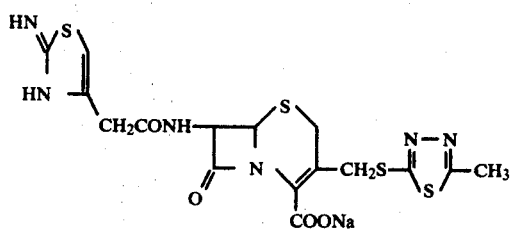

is as shown in Table 2, together with that of Cephalexin.

TABLE 2

| | Compound (A) | Cephalexin |
|---|---|---|
| S. aureus 209P | 0.39 | 1.56 |
| S. aureus 1840 | 0.78 | 12.5 |
| E. coli NIHJ JC-2 | 1.56 | 12.5 |
| K. pneumoniae DT | 0.39 | 6.25 |
| P. vulgaris Eb. 58 | 0.78 | 12.5 |
| E. coli 0-111 | 0.39 | 12.5 |

What we claim is:

1. A cephalosporon derivative of the formula:

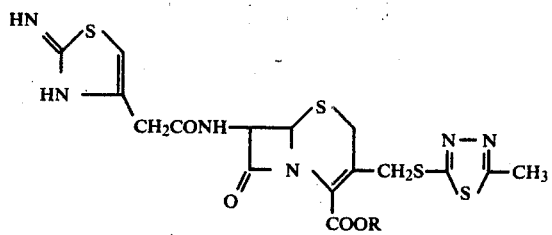

wherein R represents

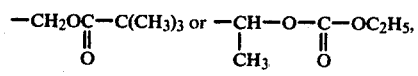

or a pharmaceutically acceptable acid addition salt thereof.

2. A cephalosporin derivative according to claim 1, namely:

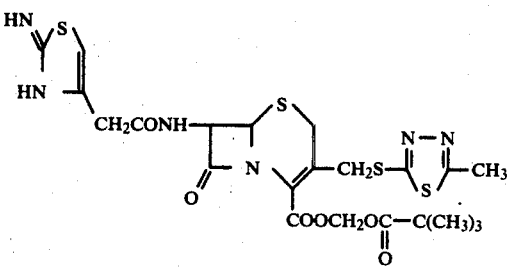

or a pharmaceutically acceptable acid addition salt thereof.

3. A cephalosporin derivative according to claim 1, namely:

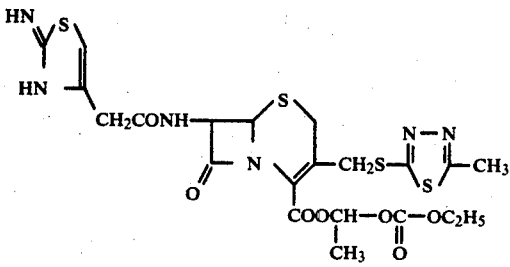

or a pharmaceutically acceptable acid addition salt thereof.

4. A pharmaceutical antibacterial composition comprising a compound of claim 2, or a pharmaceutically acceptable acid addition salt thereof, and a pharmaceutically acceptable carrier or diluent.

5. A pharmaceutical antibacterial composition comprising a compound of claim 3, or a pharmaceutically acceptable acid addition salt thereof, and a pharmaceutically acceptable carrier or diluent.

* * * * *